(12) United States Patent
Bergman et al.

(10) Patent No.: US 8,084,453 B2
(45) Date of Patent: Dec. 27, 2011

(54) ALKYL SUBSTITUTED INDOLOQUINOXALINES

(75) Inventors: Jan Bergman, Spanga (SE); Robert Engovist, Saltsjobaden (SE); Bengt Gerdin, Uppsala (SE); Ingemar Kihlstrom, Uppsala (SE); Ulf Bjorklund, Uppsala (SE)

(73) Assignee: Oxypharma AB, Stockholm (SE)

( * ) Notice: Subject to any disclaimer, the term of this patent is extended or adjusted under 35 U.S.C. 154(b) by 201 days.

(21) Appl. No.: 12/496,261

(22) Filed: Jul. 1, 2009

(65) Prior Publication Data

US 2011/0086859 A9    Apr. 14, 2011

Related U.S. Application Data

(62) Division of application No. 11/143,935, filed on Jun. 3, 2005, now Pat. No. 7,589,093.

(60) Provisional application No. 60/581,378, filed on Jun. 22, 2004.

(51) Int. Cl.
*A01N 43/58*    (2006.01)
*A01N 43/60*    (2006.01)
*A61K 31/50*    (2006.01)
*A61K 31/495*    (2006.01)

(52) U.S. Cl. ........................................ 514/250

(58) Field of Classification Search ................. None
See application file for complete search history.

(56) References Cited

U.S. PATENT DOCUMENTS 6,248,742 B1   6/2001   Bergman et al.
6,333,327 B2   12/2001  Moller et al.

FOREIGN PATENT DOCUMENTS

EP   1 261 344      12/2002
WO   0160371 A1    8/2001

OTHER PUBLICATIONS

Schiaffino et al, "Assessing Chronic Illness Representations: The Implicit Models of Illness Questionnaire", Journal of Behavioral Medicine, vol. 18, No. 6. 1995, pp. 531-548.

http://www.msakc.org/Articles/MSPain.htm; last accessed Jun. 20, 2008.
Hendershott, C.H., Processing of the American Society of Horticultural Science, (1964), 85, 201-9.
Zawadoski et al, "Synthesis of some 6-substituted derivatives of indophenazine with potential pharmacological activity", Acta Poloniae Pharmaceutica, vol. 52, No. 3, pp. 249-251 (1995).

*Primary Examiner* — Jeffrey Murray
(74) *Attorney, Agent, or Firm* — Browdy and Neimark, PLLC (57) ABSTRACT

Novel substituted indoloquinoxalines of formula (I wherein
$R^1$ is hydrogen or represents one or more similar or different substituents in the positions 7 to 10 selected from the group halogen, lower alkyl/alkoxy, hydroxy, trifluoromethyl, trichloromethyl, trifluoromethoxy,
$R^2$ represents similar or different $C_1$-$C_4$ alkyl substituents,
X is CO or $CH_2$,
Y is OH, $NH_2$, NH—$(CH_2)_n$—$R^3$ wherein $R^3$ represents lower alkyl, OH, $NH_2$, $NHR^4$ or $NR^5R^6$ wherein $R^4$, $R^5$ and $R^6$ independently are lower alkyl or cyclo-alkyl and n is an integer of from 2 to 4,
with the provision that when X is $CH_2$, Y is OH or NH—$(CH_2)_n$—OH,
and pharmacologically acceptable salts thereof are described. The compounds are useful as drugs for preventing and/or treating autoimmune diseases.

24 Claims, 5 Drawing Sheets

Fig. 1

Localization of arthritogenic epitopes on type II collagen recognized by Arthrogen-CIA® arthritogenic mAbs

Fig 2.

(B) Authentic collagen-induced arthritis

Fig. 3

Fig.4 Mean group EAE clinical scoring observed throughout the 21-day observation period.

Fig.5 Mean group EAE clinical scoring observed throughout the 21-day observation period.

ALKYL SUBSTITUTED INDOLOQUINOXALINES

The present invention relates to novel alkyl substituted indoloquinoxalines of the general formula (I)

wherein
$R^1$ is hydrogen or represents one or more similar or different substituents in the positions 7 to 10 selected from the group halogen, e.g. chloro, fluoro, bromo, lower alkyl/alkoxy, hydroxy, trifluoromethyl, trichloromethyl, trifluoromethoxy.
$R^2$ represents similar or different $C_1$-$C_4$ alkyl substituents,
X is CO or $CH_2$,
Y is OH, $NH_2$, NH—$(CH_2)_n$—$R^3$ wherein $R^3$ represents lower alkyl, OH, $NH_2$, $NHR^4$ or $NR^5R^6$ wherein $R^4$, $R^5$ and $R^6$ independently are lower alkyl or cycloalkyl and n is an integer of from 2 to 4,
with the provision that when X is $CH_2$, Y is OH or NH—$(CH_2)_n$—OH,
and pharmacologically acceptable salts thereof.

The novel alkyl substituted indoloquinoxalines of the present invention are useful as drugs and in particular for preventing and/or treating autoimmune diseases, e.g. for preventing and/or treating rheumatoid arthritis (RA) and multiple sclerosis (MS).

In this specification the term halogen means chloro, fluoro or bromo.

The term lower alkyl means linear or branched alkyl groups with 1 to 4 carbon atoms, such as methyl, ethyl, propyl, isopropyl, butyl, isobutyl, sec-butyl, tert-butyl, preferably methyl or ethyl.

The term alkoxy means linear or branched alkoxy groups with 1 to 4 carbon atoms such as methoxy, ethoxy, propoxy, isopropoxy, butoxy, isobutoxy, sec-butoxy, tert-butoxy The term cycloalkyl means $C_5$ to $C_7$ cycloalkyl groups such as cyclopentyl, cyclohexyl, cycloheptyl.

A suitable group of compounds are compounds of formula (I) wherein both $R^2$ are methyl groups.

Another suitable group of compounds are compounds of formula (I) wherein $R^1$ is a halogen group and both $R^2$ are methyl groups.

A preferred group of compounds are compounds of formula (I) wherein $R^1$ is a chloro or fluoro group.

Another preferred group of compounds are compounds of formula (I) wherein Y is $NR^5R^6$, especially when $R^5$ and $R^6$ are similar or dissimilar lower alkyl groups.

An object of the invention also relates to the compounds of formula (I) for use as drugs.

Another object of the invention is the use of the compounds of formula (I) for preventing and/or treating autoimmune diseases especially for preventing and treating rheumatoid arthritis (RA) and multiple sclerosis (MS).

The invention also relates to methods for preparing the novel alkyl substituted indoloquinoxalines.

BACKGROUND

Under certain conditions, including in certain disease states, an individual's immune system will identify its own constituents as "non-self", and initiate an immune response against "self" material, at times causing more damage or discomfort as from an invading microbe or foreign material, and producing serious illness in an individual. Autoimmune disease results when an individual's immune system attacks his or her own organs or tissues, producing a clinical condition associated with the destruction of that tissue, as exemplified by diseases such as rheumatoid arthritis (RA), insulin-dependent diabetes mellitus, acquired immuno-deficiency syndrome ("AIDS"), hemolytic anemias, rheumatic fever, Alzheimer's disease, asthma, atherosclerosis, inflammatory bowel disease, ischemic injury, Parkinson's disease, myasthenia gravis, anemia, scleroderma, Addison's disease; septic shock, psoriasis, thyroiditis, glomerulonephritis, autoimmune hepatitis, multiple sclerosis (MS), systemic lupus erythematosus (SLE), etc. Blocking, neutralizing or inhibiting the immune response, counteracting the consequences of the immune activity or removing its cause in these cases is, therefore, desirable.

It is believed that rheumatoid arthritis results from the presentation of a relevant antigen to an immunogenetically susceptible host. The antigens that could potentially initiate an immune response that results in rheumatoid arthritis might be endogenous or exogenous. Possible endogenous antigens include collagen, mucopolysaccharides and rheumatoid factors. Exogenous antigens include e.g. mycoplasms, mycobacteria, spirochetes and viruses. By-products (e.g. prostaglandins and oxygen radicals) of the immune reaction inflame the synovium and trigger destructive joint changes (e.g. collagenase). Rheumatoid arthritis (involving the destruction of the joint lining tissue) are characterized as being the result of a mostly cell-mediated autoimmune response and appear to be due primarily to the action of T-cells (see Sinha et al., Science 248:1380 (1990)).

There is a wide spectrum of disease severity, but many patients run a course of intermittent relapses and remissions with an overall pattern of slowly progressive joint destruction and deformity. The clinical manifestations may include symmetrical polyarthritis of peripheral joints with pain, tenderness, swelling and loss of function of affected joints, morning stiffness, and loss of cartilage, erosion of bone matter and subluxation of joints after persistent inflammation. Extra-articular manifestations include rheumatoid nodules, rheumatoid vasculitis, pleuro-pulmonary inflammations, scleritis, sicca syndrome, Felty's syndrome (splenomegaly and neutropenia), osteoporosis and weight loss (Katz (1985), Am. J. Med., 79:24 and Krane and Simon (1986), Advances in Rheumatology, Synderman (ed.), 70(2):263-284). The clinical manifestations will result in a high degree of morbidity resulting in disturbed daily life of the patient. Unfortunately, despite considerable investigative efforts there is no cure for RA.

Established treatments of RA are designed to inhibit either final common pathways of inflammation or immunological mediators. Both approaches are non-specific and, therefore, are associated with severe side effects. Corticosteroids have multiple effects on the immune system and other tissues. Their use is complicated by very high incidence of musculoskeletal, metabolic, neurologic and connective tissue side effects, as well as immunosuppression which may lead to life-threatening infections. For this reason, corticosteroids are usually avoided until all other forms of treatment have failed. See generally, R. Million et al., "Long-Term Study of Management of rheumatoid Arthritis", Lancet 1:812 (1984).

Cytotoxic and anti-metabolic drugs, such as methotrexate, azathioprine and cyclophosphamide are non-specifically affecting all rapidly dividing cells and therefore are associated with bone marrow and gastrointestinal toxicity and increased incidence of malignancy. In addition, methotrexate treatment of RA has been reported to induce liver damage and lung disease which may be fatal. See J. A. Engelbrecht et al., "Methotrexate Pneumonitis After Low-Dose Therapy for Rheumatoid Arthritis", Arthritis and Rheumatism 26:1275 (1983) and G. W. Cannon et al., "Acute Lung Disease Associated With Low-Dose Pulse Methotrexate Therapy In Patients With Rheumatoid Arthritis", Arthritis and Rheumatism 26:1269 (1983).

Most nonsteroidal anti-inflammatory drugs (NSAIDs) currently used are designed to non-specifically inhibit prostaglandin synthesis. NSAIDs currently in use modify or diminish—but to not arrest—the inflammatory response. Acetyl salicylic acid remains the most commonly used NSAID. Acetyl salicylic acid toxicity takes many forms, including hypersensitivity reactions, deafness, gastrointestinal and renal toxicity. See generally Simon and Mills, "Nonsteroidal Antiinflammatory Drugs", N. Eng. J. Med. 302:1179 (1980).

Gold compounds and penicillamine have also been used in the treatment of RA. They are both associated with high incidence of bone marrow, renal and mucocutaneous toxicity. Gold treatment, in particular, is associated with nephropathy, W. Katz et al., "Proteinuria in Gold-Treated Rheumatoid Arthritis", Ann. Int. Med. 101:176 (1984), Penicillamine, while questionably effective, is toxic even at relatively low doses. See W. F. Kean et al., "The Toxicity Pattern Of D-Penicillamine Therapy", Arthritis and Rheumatism 23:158 (1980). These problems have led to almost complete abandonment of these drugs in RA therapy.

Other established therapies are cyclosporin and anti-TNF.alpha-antibodies. However, serious renal toxicity and non-specific immunosuppression limit significantly the utility of cyclosporin. Due to its ubiquitous role in many cellular functions, anti-TNF therapy may not be a safe therapeutic strategy for RA. Development of lupus-like disease has been noticed in some cases. However, clinical efficacy data show promising results with the anti-TNF approach.

Thus, current therapies for RA are associated with high incidence of serious side effects. Furthermore, although some medications may offer symptomatic relief, in many cases, they do not significantly modify the progression of joint destruction. What is needed is an effective therapeutic approach with lower toxicity such that the treatment is better tolerated and more appropriate for the treatment of RA.

The present invention contemplates a new class of anti-RA drug, namely compounds that produce a reduction in the clinical signs and symptoms of the disease.

Multiple sclerosis (MS) is a disease of the central nervous system that affects the brain and spinal cord. It strikes an estimated 2.5 million people worldwide and is the major acquired neurologic disease in young adults. With destruction of the protective myelin sheath, nerve impulses are disrupted leading to a variety of neurological symptoms. Common signs and symptoms of MS include fatigue, psychological and cognitive changes, weakness or paralysis of limbs, numbness, vision problems, speech difficulties, muscle spasticity, difficulty with balance when walking or standing, bowel and bladder dysfunction, and sexual dysfunction. Approximately half the people with this disease have relapsing-remitting MS in which there are unpredictable attacks where the clinical symptoms become worse (exacerbation) which are separated by periods of remission where the symptoms stabilize or diminish. The other half have chronic progressive MS without periods of remission.

At present there are no cures for MS. Many medications are available to relieve symptoms in progressive MS. For example, corticosteroids are used to reduce inflammation in nerve tissue and shorten the duration of flare-ups; Muscle relaxants such as tizanidine (Zanaflex) and baclofen (Lioresal) are oral treatments for muscle spasticity; Antidepressant medication fluoxetine (Prozac), the antiviral drug amantadine (Symmetrel) or a medication for narcolepsy called modafinil (Provigil) are used to reduce fatigue.

A few other drugs are available for MS that are not directly related to symptom management but may act to alter the course of the disease. These drugs include beta interferons (Betaferon, Avonex, Rebif) and glatiramer acetate (Copaxone). These drugs may have an impact on the frequency and severity of relapses, and the number of lesions as seen on MRI scans. Some of the drugs appear to have an effect of slowing the progression of disability. U.S. Pat. No. 4,617,319 discloses a method of treating multiple sclerosis using 1,4-dihydroxy-5,8-bis[[(2-hydroxyethyl-amino)ethyl]amino]anthraquinone, which is also known by the generic name mitoxantrone (Novantrone).

None of these existing therapies are proven satisfactory because of limited efficacy and/or significant toxicity. In addition, many of these therapies are required to be administered frequently and some are very expensive. Thus, there clearly exists a need for novel and effective methods of treating MS.

The compounds of the present invention may be formulated for oral, parenteral (e.g. intravenous, intramuscular or subcutaneous), dermal, buccal, intranasal, sublingual or rectal administration or may be formulated for administration by inhalation or insufflation. Furthermore, the compounds according to the present invention may also be formulated for sustained delivery.

PRIOR ART

The closest prior art are the compounds described in the European patent EP 238459 and the corresponding U.S. Pat. No. 4,990,510 and the uses of said compounds described in EP 799038 and EP 1 261 344 and the corresponding U.S. Pat. No. 6,248,742, U.S. Pat. No. 6,465,466 and U.S. Pat. No. 6,333,327. Of the compounds disclosed in said patents e.g. the compound 2,3-dimethyl-6-(N,N-dimethylaminoethyl)-6H-indolo(2,3-b)quinoxaline (B 220) has been shown to be a promising compound for treating RA and MS in common tests viz. the collagen-induced arthritis (CIA) model and the EAE model, respectively. However, the compounds according to the present invention have a surprisingly improved effect against RA and MS in comparison with B220.

The novel compounds according to the invention can be prepared by the following general procedures:

The anions of indolo[2,3-b]quinoxalines of formula (a) generated by treatment with a suitable base, such as sodium hydride (NaH), potassium t-butoxide or potassium hydroxide in a two-phase system

(a)

are alkylated by α-halogenated alkylnitriles or α-halogenated alkyl esters, e.g. chloroacetonitrile and methyl or ethyl bromoacetate respectively, whereby 6-cyanomethylindolo[2,3-b]quinoxalines of formula (b)

(b)

and indolo[2,3-b]quinoxaline-6-yl-acetic acid (c; $R^7$=H) or its salts (e.g. Na) and alkyl indolo[2,3-b]quinoxaline-6-yl-acetates of formula (c)

(c)

wherein $R^7$ is methyl or ethyl, respectively are obtained. The primary amides, indolo[2,3-b]quinoxaline-6-yl-acet-amides of formula (II)

(II)

are thereafter formed by an acidic hydrolysis of the compounds of formula (b) in a strong acid such as sulfuric acid. The secondary amides of formula (III)

(III)

are made by condensation of the alkyl esters of formula (c) with an excess of the appropriate amine with or without a solvent.

EXAMPLES

In the following experiments the measurements were carried out by means of the following apparatuses and conditions.

NMR spectra were recorded in DMSO-$d_6$ solutions at room temperature and using the signal from DMSO-$d_6$ (1H: δ=2.50 ppm; $^{13}$C: δ=39.5) as internal standard, on a Bruker DPX 300 (300 MHz) spectrometer. δ values are given in ppm. Melting points were taken on a Büchi Melting Point B-545 apparatus and are uncorrected. Solvents were of analytical grade and were used as received.

An indolo[2,3-b]quinoxaline derivative of the formula (a) (1 eq.) is added portionwise to a slurry of NaH (1.1 eq.) in N,N-dimethylacetamide (DMA), N,N-dimethylformamide (DMF) or DMSO (5 mL/1 mmol of compound a) at 30° C. under an inert atmosphere (Ar or $N_2$) and stirred for 30 min. Chloroacetonitrile (1.1 eq.) is added in one portion. The resulting reaction mixture is stirred for 20 h at room temperature. The reaction mixture was finally poured into water, filtered, washed with water and dried to give a compound of formula (b).

When $R^1$ is chloro in formula (a) the following compound of formula (b) is obtained, i.e. the product 9-chloro-2,3-dimethyl-6-cyanomethyl-6H-indolo[2,3-b]quinoxaline.

Yield: 98%; Mp: 286-288° C.; $^1$H-NMR δ: 8.36 (d, 1H), 8.04 (s, 1H), 7.99-9.94 (m, 2H), 7.86 (dd, 1H), 5.75 (s, 2H), 2.53 (s, 6H).

The novel compounds according to the present invention which are primary amides of the formula (II)

(II)

can be prepared according to the following procedure:

A compound of formula b is dissolved in $H_2SO_4$ (conc., 10 mL/1 g b) and is thereafter poured out on ice-water and stirred for 5 min. The solid thus formed is collected and washed with water. The dried solid is treated with hot $CH_2Cl_2$, filtered and washed with more $CH_2Cl_2$ and dried to give a compound of formula (II).

The following compounds were prepared in this manner:

Compound A 2,3-Dimethylindolo[2,3-b]quinoxaline-6-yl-acetamide ($R^1$H, $R^2$=$CH_3$, X=CO, Y=$NH_2$)

Yield: 72%; $^1$H-NMR δ: 8.38 (d, 1H), 8.16 (s, 1H), 8.05 (s, 1H), 7.70 (m, 2H), 7.59 (d, 1H), 7.40 (t, 1H), 7.16 (s, 1H), 5.08 (s, 2H), 2.50 (s, 6H);

Compound B

9-Chloro-2,3-dimethyl-indolo[2,3-b]quinoxaline-6-yl-acetamide ($R^1$=$C^1$, $R^2$=$CH_3$, X=CO, Y=$NH_2$)

Yield: 66%; $^1$H-NMR δ: 8.29 (s, 1H), 7.99 (s, 1H), 7.90 (s, 1H), 7.65-7.50 (m, 3H), 7.07 (bs, 1H), 5.06 (s, 2H), 2.48 (s, 6H);

Compound C 2,3-Dimethyl-9-fluoro-indolo[2,3-b]quinoxaline-6-yl-acetamide ($R^1$=F, $R^2$=$CH_3$, X=CO, Y=$NH_2$)

Yield: 32%; Mp: 316-319° C.; $^1$H-NMR δ: 8.11 (dd, 1H), 8.01 (s, 1H), 7.86 (s, 1H), 7.70 (s, 1H), 7.65-7.55 (m, 2H), 7.29 (s, 1H), 5.05 (s, 2H), 2.50 (s, 6H).

The new secondary amides of the formula (III) according to the present invention (III)

can be prepared by the following procedure:

An indolo[2,3-b]quinoxaline derivative of formula a (1 eq.) is added portionwise to a slurry of NaH (1.1 eq.) in DMA, DMF or DMSO (5 mL/1 mmol a) at 30° C. under an inert atmosphere (Ar or $N_2$) and stirred for 30 min. Alkyl bromoacetate (1.1 eq.) is added in one portion. The resulting reaction mixture is stirred for 20 h at room temperature. The reaction mixture is then poured into water, filtered, washed with water and dried to give a product of formula (c).

When methyl bromoacetate is used as the alkyl bromoacetate and $R^1$ is 9-fluoro and $R^2$ is methyl the following product of formula (c) is obtained:

Methyl-2,3-dimethyl-9-fluoro-indolo[2,3-b]quinoxaline-6-yl-acetate

Yield: 74%; Mp: 257-259° C.; $^1$H-NMR δ: 8.16 (dd, 1H), 8.05 (s, 1H), 7.91 (s, 1H), 7.82 (dd, 1H), 7.62 (dt, 1H), 5.41 (s, 2H), 3.65 (s, 3H), 2.50 (s, 6H).

The secondary amides of formula (III) are then obtained by means of the following procedure:

A compound of formula c is added to the appropriate amine (10 mL/0.5 g c) at reflux and is finally refluxed for 4-15 min. The reaction mixture is allowed to cool to room temperature whereupon water is added. The solid formed is filtered and washed with water, dried and treated with hot ethanol and filtered, and again washed with ethanol and dried to give a product of formula (III).

The following compounds were prepared in this manner:

Compound D 2,3-Dimethyl-6-(N,N-dimethylaminoethylamino-2-oxoethyl)-6H-indolo[2,3-b]quinoxaline ($R^1$=H, $R^2$=$CH_3$, X=CO, Y=NH—$CH_2$—$CH_2$—$R^3$; $R^3$=$NR^5R^6$; $R^5$=$R^6$=$CH_3$)

Yield: 63%; $^1$H-NMR δ: 8.33 (d, 1H), 8.27 (t, 1H), 8.02 (s, 1H), 7.85 (s, 1H), 7.70 (t, 1H), 7.58 (d, 1H), 7.39 (t, 1H), 5.09 (s, 2H), 3.17 (q, 2H), 2.49 (s, 6H), 2.32 (t, 2H), 2.14 (s, 6H);

Compound E

9-Chloro-2,3-dimethyl-6-(N,N-dimethylaminoethylamino-2-oxoethyl)-6H-indolo-[2,3-b]quinoxaline ($R^1$=Cl, $R^2$=$CH_3$, X=CO, Y=NH—$CH_2$—$CH_2$—$R^3$; $R^3$=$NR^5R^6$; $R^5$=$R^6$=$CH_3$)

Yield: 58%; $^1$H-NMR δ: 8.29 (d, 1H), 8.23 (t, 1H), 7.98 (s, 1H), 7.82 (s, 1H), 7.71 (dd, 1H), 7.61 (d, 1H), 5.09 (s, 2H), 3.16 (q, 2H), 2.47 (s, 6H), 2.28 (t, 2H), 2.12 (s, 6H);

Compound F

9-Chloro-2,3-dimethyl-6-(aminoethylamino-2-oxoethyl)-6H-indolo[2,3-b]quinoxaline ($R^1$=$C^1$, $R^2$=$CH_3$, X=CO, Y=NH—$CH_2$—$CH_2$—$NH_2$)

Yield: 71%; $^1$H-NMR δ: 8.32 (d, 1H), 8.27 (t, 1H), 8.01 (s, 1H), 7.85 (s, 1H), 7.73 (dd, 1H), 7.66 (d, 1H), 5.11 (s, 1H), 3.17 (s, 2H), 3.07 (q, 2H), 2.57 (t, 2H), 2.49 (s, 6H);

Compound G 2,3-Dimethyl-6-(N,N-dimethylaminoethylamino-2-oxoethyl)-9-fluoro-6H-indolo-[2,3-b]quinoxaline ($R^1$=F, $R^2$=$CH_3$, X=CO, Y=NH—$CH_2$—$CH_2$—$R^3$; $R^3$=$NR^5R^6$, $R^5$=$R^6$=$CH_3$)

Yield: 51%; Mp: 241-242° C.; $^1$H-NMR δ: 8.10-8.00 (m, 3H), 7.84 (s, 1H), 7.59-7.53 (m, 2H), 5.09 (s, 2H), 3.19 (q, 2H), 2.94 (s, 1H), 2.79 (s, 1H), 2.50 (s, 6H), 2.31 (t, 2H), 2.14 (s, 6H);

Compound H 2,3-Dimethyl-6-(aminoethylamino-2-oxoethyl)-9-fluoro-6H-indolo[2,3-b]quinoxaline ($R^1$=F, $R^2$=$CH_3$, X=CO, Y=NH—$CH_2$—$CH_2$—$NH_2$)

Yield: 88%; Mp: 269-271° C.; $^1$H-NMR δ: 8.26 (t, 1H), 8.13 (dd, 1H), 8.04 (s, 1H), 7.88 (s, 1H), 7.68-7.56 (m, 2H), 5.12 (s, 2H), 3.07 (q, 2H), 2.57 (t, 2H), 2.50 (s, 6H).

The New Secondary Amides of Formula (IV)

(IV)

wherein $R^1$, $R^2$, $R^3$, $R^5$ and $R^6$ and n are as defined in formula (I)

can also be prepared by the following general alternative method as the following example illustrates:

The corresponding indolo[2,3-b]quinoxaline derivative (formula a) (1 eq.) was added portionwise to a slurry of NaH (3 eq.) in DMA or DMSO (5 mL/1 mmol formula a) at 30° C. under an inert atmosphere (Ar or $N_2$) and stirred for 30 min. 2-Chloro-N-(2-dimethylaminoethyl)acetamide hydrochloride (1.5 eq.) (This alkylation reagent was prepared as described by Sanchez et al., J. Heterocycl. Chem., 31: 297-304 (1994)) was added in one portion. The resulting reaction mixture was stirred for 20 h at 40° C. and then poured into water, filtered, washed with water and dried. The solid was acidified by treatment with hydrochloric acid and thereafter filtered. The filtrate was basified by treatment with sodium hydroxide and the solid formed was isolated by filtration, washed with water and dried.

Compound J 2,3-Dimethyl-6-(N,N-dimethylaminoethylamino-2-oxoethyl)-9-fluoro-6H-indolo[2,3-b]quinoxaline Yield: 89%; Mp: 242-243° C.

The New Carboxylic Acid of the Formula (V)

(V)

wherein $R^1$ and $R^2$ are as defined in formula (I)

can be prepared according to the following procedure:

General Procedure

The appropriate indolo[2,3-b]quinoxaline derivative of the formula (a) (1 eq.) was added portionwise to a slurry of NaH (1.1 eq.) in DMA or DMSO (5 mL/1 mmol a) at 30° C. under an inert atmosphere (Ar or $N_2$) and stirred for 30 minutes, whereupon sodium chloroacetate (1.1 eq.) was added in one portion. The resulting reaction mixture was stirred for 20 h at room temperature and finally poured into water, acidified with HCl, filtered, washed with water, dried and recrystallized (DMF).

Compound K 2,3-Dimethyl-9-chloro-indolo[2,3-b]quinoxaline-6-yl acetic acid

Yield: 0.77 g (45%); $^1$H-NMR δ 13.29 (bs, 1H), 8.34 (s, 1H), 8.03 (s, 1H), 7.89 (s, 1H), 7.83-7.75 (m, 2H), 5.26 (s, 2H), 2.50 (s, 6H); Mp: 331-332° C.

The new carboxylic acid of the formula (V) wherein $R^1$ and $R^2$ are as defined in formula (I) can also be prepared by the general alternative method as the following example illustrates:

Methyl 2,3-dimethyl-9-fluoro-indolo[2,3-b]quinoxalin-6-yl acetate (1.65 g) was stirred in ethanol (30 mL) with aq. NaOH (5%; 30 mL) for 24 h. The reaction mixture was acidified with aq. HCl (1M). The solid thus formed was filtered, washed with water and dried.

Compound L 2,3-dimethyl-9-fluoro-indolo[2,3-b]quinoxaline-6-yl-acetic acid

Yield: 1.54 g (97%); $^1$H-NMR δ: 14-13 (bs, 1H), 8.06 (dd, 1H), 7.93 (s, 1H), 7.80 (s, 1H), 7.75 (dd, 1H), 7.56 (m, 1H), 5.21 (s, 2H), 2.43 (s, 6H); Mp: 317-318° C.

The compounds according to the present invention were tested according to the following models for evaluation of the effect against rheumatoid arthritis and against multiple sclerosis.

Collagen-induced arthritis (CIA) in mice is widely used as an experimental model for rheumatoid arthritis (RA) in humans. CIA is mediated by autoantibodies which bind to a particular region of type II collagen, such as CB11 (CNBr-digested fragment of type II collagen).

Antibody-mediated CIA can be induced by iv injection of a combination of 4 different monoclonal antibodies (Arthrogen-CIA® mAb) generated by Arthrogen-CIA® mouse B-hybridoma cell lines.

Figure 1:
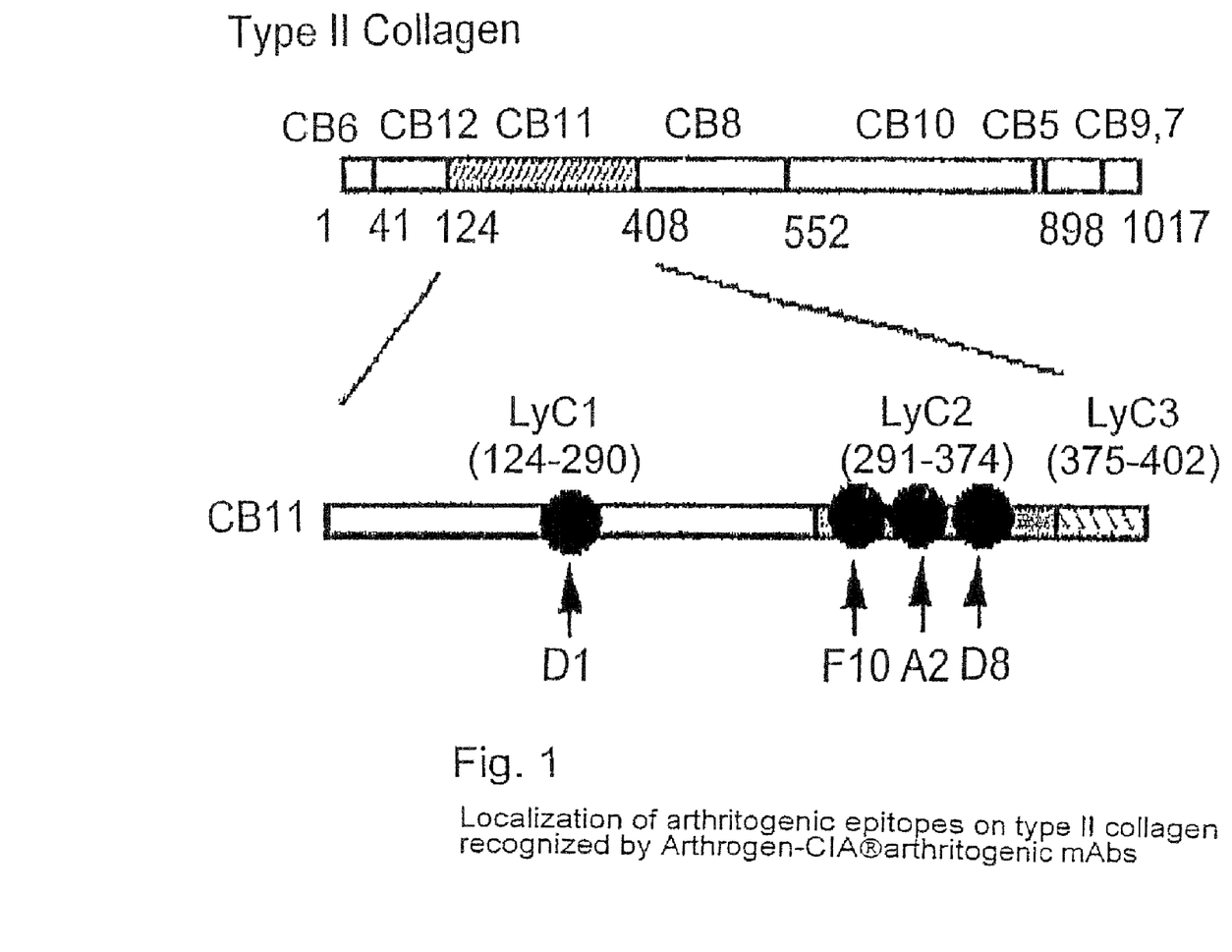
FIG. 1 discloses localization of arthritogenic epitopes on type II collagen.

Three of the mAbs recognize autoantigenic epitopes clustered within an 84 amino acid residue fragment, LyC2 (the smallest arthritogenic fragment of type II collagen) of CB11 and the fourth mAb reacts with LyC1 (FIG. 1). Importantly, all 4 mAbs recognize the conserved epitopes shared by various species of type II collagen and crossreact with homologous and heterologous type II collagen.

A cocktail of 4 monoclonal antibodies are used. These arthritogenic mAbs alone or in combination with bacterial LPS can induce severe arthritis within days instead of weeks (classic CIA model).

Reference is made to FIG. 1.

1. Advantages of the Antibody-Induced Arthritis Model
    Arthritis develops in mice within 24-48 hr after an iv. injection of arthritogenic mAbs alone or after an injection of LPS following a subarthritogenic dose of mAbs. In both cases, arthritis persists for at least 2-3 weeks or more and leads to ankylosis.
    Arthritis is induced not only in CIA-susceptible DBA/1 and B10.RIII mice, but also in some CIA-resistant mice, such as Balb/c.
    This model is ideal for screening anti-inflammatory therapeutic agents.
    This model is ideal for studying inflammatory mediators such as cytokines, chemokines and metalloproteinases and other factors such as the role of bacterial flora and their by-products in triggering and exacerbating arthritis.

Comparison of Authentic CIA and mAb-LPS Induced Arthritis.

Figure 2:
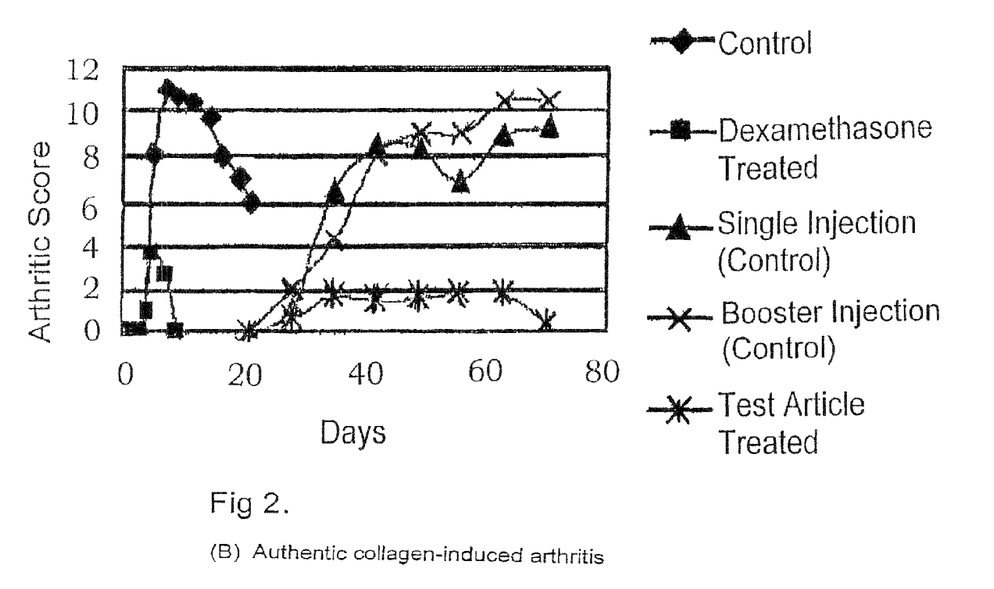
FIG. 2 is a graph of arthritic score measurement.

(A) A cocktail of 4 monoclonal antibodies to type II collagen (2 mg) is injected intravenously on day 0 followed by an intraperitoneal injection of LPS (50 μg) on day 3. Arthritis will develop on day 4 and reach its peak on day 7-8. The therapeutic effects of test compounds will be determined on day 7. Osteoblast formation and bone degradation will be more significant on day 14 and day 21 (not shown).

(B) Authentic collagen-induced arthritis.

Reference is made to FIG. 2.

Figure 3:
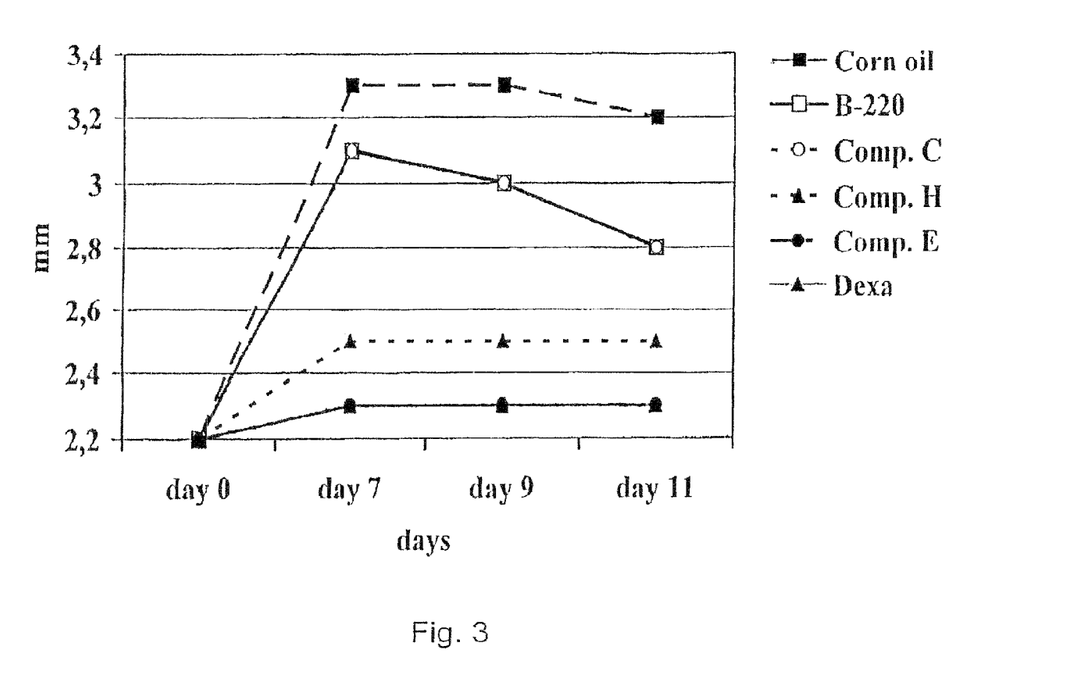
FIG. 3 is a graph of mean group values (mm) of hind paw thickness measured throughout 11-observation term.

Measurement of arthritis. Hind paw thickness, left and right of each animal (9 animals in each group) was measured in mm on study days 0 (base-line), 7, 9 and 11 using a Mitutoyo Electronic Digital Caliper. Hind paw thickness in animals after administration of Compound H, Compound E and Dexamethasone (positive control) was found to be highly significant lower vs vehicle control (corn oil). Dexamethasone is a cortisone which suppresses inflammation and normal immune response, and is used systemically and locally to treat inflammatory disorders. Patients are for safety reasons treated with short courses of cortisones to bring the inflammation under control in the window between starting the DMARD or DMARD combination and the likely response time.

|  | day 0 | day 7 | day 9 | day 11 |
| --- | --- | --- | --- | --- |
| Corn oil | 2.2 | 3.3 | 3.3 | 3.2 |
| B-220 | 2.2 | 3.1 | 3.0 | 2.8 |
| Comp. C | 2.2 | 3.1 | 3.0 | 2.8 |
| Comp. H | 2.2 | 2.5 | 2.5 | 2.5 |
| Comp. E | 2.2 | 2.3 | 2.3 | 2.3 |
| Dexamethasone | 2.2 | 2.3 | 2.3 | 2.3 |

Reference is made to FIG. 3.

Note: The curves for compound E and Dexamethasone (Dexa) and the curves for B 220 and compound C, respectively overlap each other.

FIG. 3. Mean group values (mm) of hind paw thickness measured throughout the entire 11-day observation period in the mAB/LPS-induced arthritic mice following once daily (day 0-5) repeated subcutaneous administration of B-220 analogues, Dexamethasone (positive control) or corn oil (negative control).

Studies using a mouse model of MS, experimental allergic encephalomyelitis (EAE) (Alvord, E. C., et al., Prog. Clin. Biol. Res. 146:1-8 (1984); Swanborg, R. H., Clin. Immunol. Immunopathol. 77:4-13 (1995); Martin, R. and McFarland, H. F., Crit. Rev. Clin. Lab. Sciences 32:121-182 (1995)), have been useful in characterizing the immune response in a disease similar to MS. EAE can be induced in several strains of mice by subcutaneous (s.c.) injection of myelin proteins such as myelin basic protein (MBP) or proteolipid proteins (PLP) in the presence of Freund's adjuvant. Adoptive transfer studies in the EAE model demonstrated that CD4+ T cells from mice immunized with MBP or PLP could transfer disease to naive mice suggesting that EAE is a T cell-mediated disease.

The results presented are generated in the EAE model as follows: The model consists of a sensitization period, induced by the single subcutaneous (SC) injection of PLP emulsified in Complete Freund's Adjuvant (CFA) on day 0 of the study, followed by intraperitoneal supplemental immunostimulation with Pertussis Toxin och day 0 and 48 hours later. The test items were administered by 1× daily repeated dosing sessions throughout 10 successive treatment days (days 0-9). However, Copaxone was administered every two days from day 0 to day 18 i.e. 10 administrations, cf. FIG. 5. All animals (10 in each group) were examined for signs of any neurological responses and symptoms prior to EAE induction (day 0) and thereafter on a daily basis throughout the 21-day observation period. EAE reactions were scored and recorded according to a classical 0-5 scale in ascending order of severity (grade 0, normal to grade 5 moribund and/or death).

Figure 4:
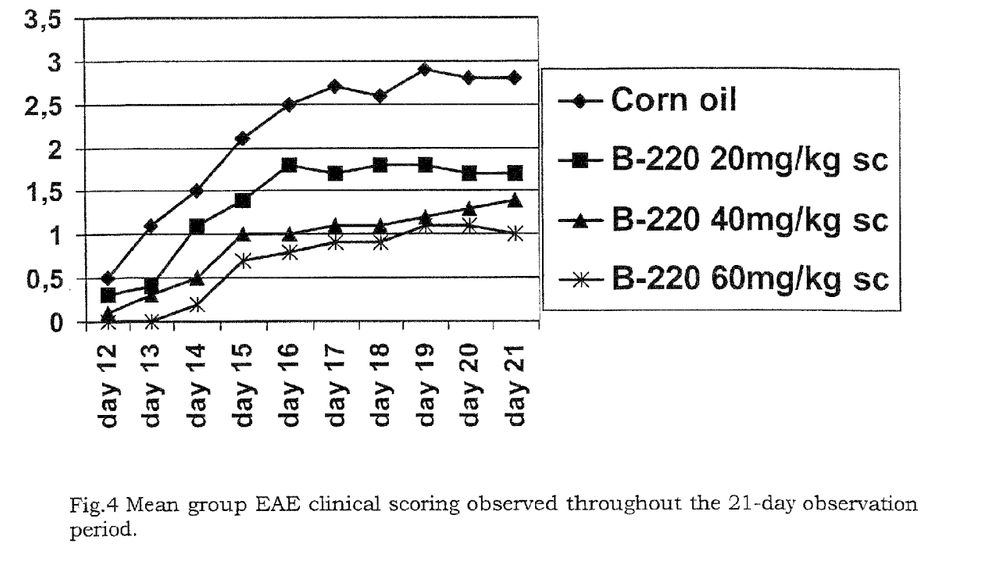
FIG. 4 is a graph of mean group EAE clinical scoring observed through days 12 through 21; and, FIG. 5 is a graph of mean group EAE clinical scoring observed through days 9-21.

Reference is made to FIG. 4.

FIG. 4 Mean group EAE clinical scoring observed throughout the 21-day observation period.

Figure 5:
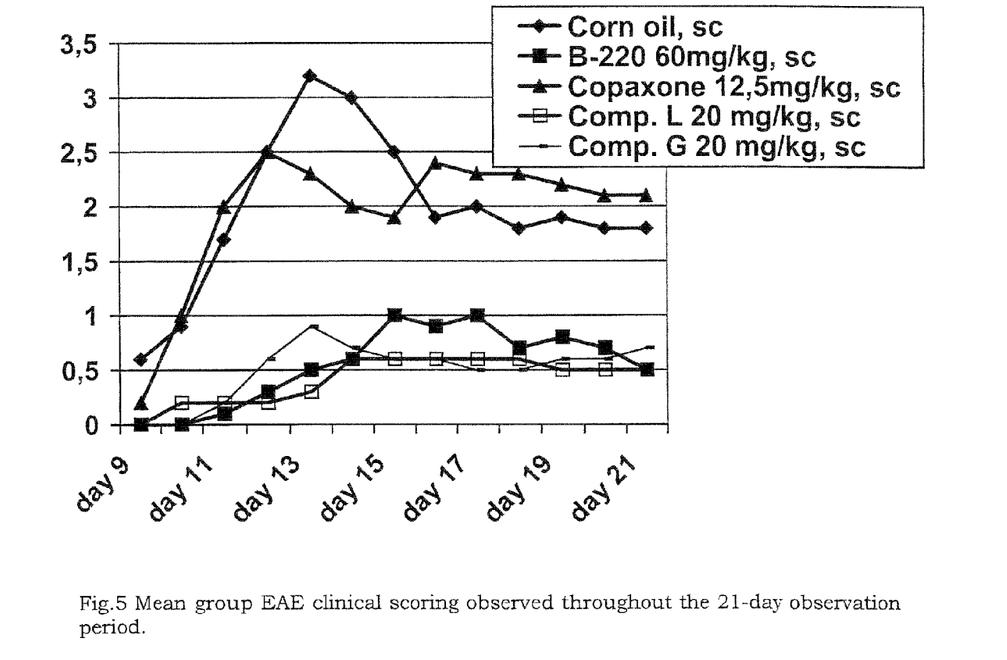

Reference is made to FIG. 5

FIG. 5 Mean group EAE clinical scoring observed throughout the 21-day observation period.

What is claimed is:

1. A method for the treatment of an autoimmune disease selected from rheumatoid arthritis and multiple sclerosis, comprising
administering to a patient in need thereof an autoimmune-effective amount of a compound of formula (I)

wherein
$R^1$ is hydrogen or represents one or more similar or different substituents in the positions 7 to 10 selected from the group halogen, lower alkyl/alkoxy, hydroxy, trifluoromethyl, trichloromethyl, trifluoromethoxy,
$R^2$ represents similar or different $C_1$-$C_4$ alkyl substituents,
X is CO or $CH_2$,
Y is OH, $NH_2$, NH—$(CH_2)_n$—$R^3$ wherein $R^3$ represents lower alkyl, OH, $NH_2$, $NHR^4$ or $NR^5R^6$ wherein $R^4$, $R^5$ and $R^6$ independently are lower alkyl or cyclo-alkyl and n is an integer of from 2 to 4,
with the provision that when X is $CH_2$, Y is OH or NH—$(CH_2)_n$—OH,
or a pharmacologically acceptable salt thereof.

2. A method according to claim 1, wherein said patient is a patient suffering from rheumatoid arthritis.

3. A method according to claim 1, wherein said patient is a patient suffering from multiple sclerosis.

4. A method according to claim 1 wherein, in said compound, X is CO and Y is OH or $NH_2$ and $R^1$ is a halogen atom.

5. A method according to claim 1 wherein, in said compound, X is CO and Y is NH—$CH_2$—$CH_2$—$R^3$ wherein $R^3$ is $NH_2$ or $N(CH_3)_2$ wherein $R^1$ is a chloro or fluoro atom.

6. A method according to claim 1 wherein, in said compound, X is CO and Y is NH—$CH_2$—$CH_2$—$R^3$ wherein $R^3$ is $NH_2$ or $N(CH_3)_2$.

7. A method according to claim 1 wherein, in said compound, $R^2$ is methyl in positions 2 and 3.

8. The method of claim 1 wherein the compound is in the form of a composition further comprising one or more pharmaceutically acceptable solvents, carriers or adjuvants.

9. The method of claim 1 wherein the compound is 9-Chloro-2,3-dimethyl-6-(N,N-dimethylaminoethylamino-2-oxoethyl)-6H-indolo-[2,3-b]quinoxaline or a pharmaceutically acceptable salt thereof.

10. The method of claim 2 wherein, in said compound, X is CO and Y is OH or $NH_2$ and $R^1$ is a halogen atom.

11. The method of claim 2 wherein, in said compound, X is CO and Y is NH—$CH_2$—$CH_2$—$R^3$ wherein $R^3$ is $NH_2$ or $N(CH_3)_2$ wherein $R^1$ is a chloro or fluoro atom.

12. The method of claim 2 wherein, in said compound, X is CO and Y is NH—$CH_2$—$CH_2$—$R^3$ wherein $R^3$ is $NH_2$ or $N(CH_3)_2$.

13. The method of claim 2 wherein, in said compound, $R^2$ is methyl in positions 2 and 3.

14. The method of claim 2 wherein the compound is in the form of a composition further comprising one or more pharmaceutically acceptable solvents, carriers or adjuvants.

15. The method of claim 2 wherein the compound is selected from the group consisting of 2,3-Dimethylindolo[2,3-b]quinoxaline-6-yl-acetamide; 9-Chloro-2,3-dimethyl-indolo[2,3-b]quinoxaline-6-yl-acetamide; 2,3-Dimethyl-9-fluoro-indolo[2,3-b]quinoxaline-6-yl-acetamide; 2,3-Dimethyl-6-(N,N-dimethylaminoethylamino-2-oxoethyl)-6H-indolo[2,3-b]q-uinoxaline; 9-Chloro-2,3-dimethyl-6-(N,N-dimethylaminoethylamino-2-oxoethyl)-6H-indol-o[2,3-b]quinoxaline; 9-Chloro-2,3-dimethyl-6-(aminoethylamino-2-oxoethyl)-6H-indolo[2,3-b]quinoxaline; 2,3-Dimethyl-6-(aminoethylamino-2-oxoethyl)-9-fluoro-6H-indolo[2,3-b]quinoxaline; 2,3-Dimethyl-6-(N,N-dimethylaminoethylamino-2-oxoethyl)-9-fluoro-6H-indolo[2,3-b]quinoxaline; 2,3-Dimethyl-9-chloro-indolo[2,3-b]quinoxaline-6-yl acetic acid; and 2,3-dimethyl-9-fluoro-indolo[2,3-b]quinoxaline-6-yl-acetic acid, or a pharmaceutically acceptable salt thereof.

16. The method of claim 2 wherein the compound is 9-Chloro-2,3-dimethyl-6-(N,N-dimethylaminoethylamino-2-oxoethyl)-6H-indol-o-[2,3-b]quinoxaline or a pharmaceutically acceptable salt thereof.

17. The method of claim 3 wherein, in said compound, X is CO and Y is OH or $NH_2$ and $R^1$ is a halogen atom.

18. The method of claim 3 wherein, in said compound, X is CO and Y is NH—$CH_2$—$CH_2$—$R^3$ wherein $R^3$ is $NH_2$ or $N(CH_3)_2$ wherein $R^1$ is a chloro or fluoro atom.

19. The method of claim 3 wherein, in said compound, X is CO and Y is NH—$CH_2$—$CH_2$—$R^3$ wherein $R^3$ is $NH_2$ or $N(CH_3)_2$.

20. The method of claim 3 wherein, in said compound, $R^2$ is methyl in positions 2 and 3.

21. The method of claim 3 wherein the compound is selected from the group consisting of 2,3-Dimethylindolo[2,3-b]quinoxaline-6-yl-acetamide; 9-Chloro-2,3-dimethyl-indolo[2,3-b]quinoxaline-6-yl-acetamide; 2,3-Dimethyl-9-fluoro-indolo[2,3-b]quinoxaline-6-yl-acetamide; 2,3-Dimethyl-6-(N,N-dimethylaminoethylamino-2-oxoethyl)-6H-indolo[2,3-b]q-uinoxaline; 9-Chloro-2,3-dimethyl-6-(N,N-dimethylaminoethylamino-2-oxoethyl)-6H-indol-o[2,3-b]quinoxaline; 9-Chloro-2,3-dimethyl-6-(aminoethylamino-2-oxoethyl)-6H-indolo[2,3b]quinoxaline; 2,3-Dimethyl-6-(aminoethylamino-2-oxoethyl)-9-fluoro-6H-indolo[2,3-b]quinoxaline; 2,3-Dimethyl-6-(N,N-dimethylaminoethylamino-2-oxoethyl)-9-fluoro-6H-indolo[2,3-b]quinoxaline; 2,3-Dimethyl-9-chloro-indolo[2,3-b]quinoxaline-6-yl acetic acid; and 2,3-dimethyl-9-fluoro-indolo[2,3-b]quinoxaline-6-yl-acetic acid, or a pharmaceutically acceptable salt thereof.

22. The method of claim 3 wherein the compound is 9-Chloro-2,3-dimethyl-6-(N,N-dimethylaminoethylamino-2-oxoethyl)-6H-indol-o[2,3-b]quinoxaline or a pharmaceutically acceptable salt thereof.

23. The method of claim 3 wherein the compound is in the form of a composition further comprising one or more pharmaceutically acceptable solvents, carriers or adjuvants.

24. The method of claim 1 wherein the compound is selected from the group consisting of 2,3-Dimethylindolo[2,3-b]quinoxaline-6-yl-acetamide; 9-Chloro-2,3-dimethyl-indolo[2,3-b]quinoxaline-6-yl-acetamide; 2,3-Dimethyl-9- fluoro-indolo[2,3-b]quinoxaline-6-yl-acetamide; 2,3-Dimethyl-6-(N,N-dimethylaminoethylamino-2-oxoethyl)-6H-indolo[2,3-b]q-uinoxaline; 9-Chloro-2,3-dimethyl-6-(N,N-dimethylaminoethylamino-2-oxoethyl)-6H-indol-o[2,3-b]quinoxaline; 9-Chloro-2,3-dimethyl-6-(aminoethylamino-2-oxoethyl)-6H-indolo[2,3-b]quinoxaline; 2,3-Dimethyl-6-(aminoethylamino-2-oxoethyl)-9-fluoro-6H-indolo[2,3-b]quinoxaline; 2,3-Dimethyl-6-(N,N-dimethylaminoethylamino-2-oxoethyl)-9-fluoro-6H-indolo[2,3-b]quinoxaline; 2,3-Dimethyl-9-chloro-indolo[2,3-b]quinoxaline-6-yl acetic acid; and 2,3-dimethyl-9-fluoro-indolo[2,3-b]quinoxaline-6-yl-acetic acid, or a pharmaceutically acceptable salt thereof.

* * * * *